United States Patent
Quist et al.

(10) Patent No.: US 9,297,684 B2
(45) Date of Patent: Mar. 29, 2016

(54) ESTIMATING FLOW RATES OF A LIQUID IN A CONDUIT

(71) Applicant: Hadronex, Inc., Escondido, CA (US)

(72) Inventors: Gregory M. Quist, Escondido, CA (US); David A. Drake, Escondido, CA (US); Lawrence B. Merchell, Escondido, CA (US); Justin H. Hobbs, Escondido, CA (US)

(73) Assignee: HADRONEX, INC., Escondido, CA (US)

( * ) Notice: Subject to any disclaimer, the term of this patent is extended or adjusted under 35 U.S.C. 154(b) by 471 days.

(21) Appl. No.: 14/017,278

(22) Filed: Sep. 3, 2013

(65) Prior Publication Data

US 2015/0066396 A1    Mar. 5, 2015

(51) Int. Cl.

| | |
|---|---|
| *G01F 1/05* | (2006.01) |
| *G01P 3/36* | (2006.01) |
| *G01F 1/66* | (2006.01) |
| *G01F 15/06* | (2006.01) |
| *G01F 1/74* | (2006.01) |
| *G01F 1/00* | (2006.01) |
| G01F 25/00 | (2006.01) |
| G01P 5/24 | (2006.01) |
| G05D 7/06 | (2006.01) |

(52) U.S. Cl.
CPC .............. *G01F 15/063* (2013.01); *G01F 1/002* (2013.01); *G01F 1/667* (2013.01); *G01F 1/74* (2013.01); *G01F 25/0007* (2013.01); *G01N 2291/02836* (2013.01); *G01P 5/245* (2013.01); *G01P 5/247* (2013.01); *G05D 7/0635* (2013.01)

(58) Field of Classification Search
CPC ................................ G01F 15/063; G01F 1/002
USPC ............. 702/12, 45, 6, 13, 48; 700/282, 283; 128/204.21, 204.22, 204.23; 73/861.28, 861.41, 195; 166/305.1
See application file for complete search history.

(56) References Cited

U.S. PATENT DOCUMENTS

| | | | | |
|---|---|---|---|---|
| 5,627,749 A | * | 5/1997 | Waterman | E21B 47/00 166/902 |
| 6,158,288 A | * | 12/2000 | Smith | G01F 1/667 73/861.18 |
| 6,280,408 B1 | * | 8/2001 | Sipin | A61M 5/1483 604/65 |
| 6,618,677 B1 | * | 9/2003 | Brown | E21B 47/1005 702/13 |
| 6,920,395 B2 | * | 7/2005 | Brown | E21B 47/1005 702/13 |
| 7,096,128 B2 | * | 8/2006 | Saylor | E03F 7/00 702/33 |
| 7,172,688 B2 | * | 2/2007 | Petersen | B01D 17/0205 210/104 |

(Continued)

*Primary Examiner* — Carol S Tsai
(74) *Attorney, Agent, or Firm* — Jonathan A. Kidney; TechLaw LLP (57) ABSTRACT

In one embodiment, a flow-estimation processor receives one or more flow-depth measurements with each flow-depth measurement having been taken at a respective time. The processor calculates a respective estimated flow rate for each of the times based on the corresponding flow-depth measurement and one or more flow-estimation parameters each set to a respective initial value. The processor outputs the estimated flow rates for presentation via a user interface, and receives via the user interface one or more updated values corresponding respectively to a flow-estimation parameter. The processor calculates an updated estimated flow rate for each of the one or more times, such that each respective updated estimated flow rate is calculated based on the received updated values. The processor then outputs the updated estimated flow rates for presentation via the user interface.

20 Claims, 11 Drawing Sheets

(56) References Cited

U.S. PATENT DOCUMENTS

| | | | | |
|---|---|---|---|---|
| 7,991,510 B2* | 8/2011 | Duan | G01F 1/667 | 700/282 |
| 8,489,342 B2* | 7/2013 | Dugger | G01F 1/667 | 702/45 |
| 8,589,090 B2* | 11/2013 | Ruiter | A61M 5/14212 | 702/45 |
| 2004/0006429 A1* | 1/2004 | Brown | E21B 47/1005 | 702/12 |
| 2007/0191990 A1* | 8/2007 | Duan | G01F 1/667 | 700/282 |
| 2007/0289536 A1* | 12/2007 | Dunn | A01J 5/01 | 119/14.14 |
| 2009/0281671 A1* | 11/2009 | Duan | G01F 1/667 | 700/282 |
| 2012/0053861 A1* | 3/2012 | Kremer | C10G 75/02 | 702/50 |
| 2012/0211228 A1* | 8/2012 | Troshko | E21B 43/124 | 166/305.1 |
| 2012/0269381 A1* | 10/2012 | Choo | G08B 21/18 | 382/100 |
| 2013/0080081 A1* | 3/2013 | Dugger | G01F 1/667 | 702/48 |
| 2014/0069207 A1* | 3/2014 | Leaders | G01F 1/667 | 73/861.28 |

* cited by examiner

ESTIMATING FLOW RATES OF A LIQUID IN A CONDUIT

BACKGROUND

A water management system (e.g., wastewater or storm water) is generally used to accomplish the transfer or transport of sewage from some residences and business in a community to a water-treatment plant that cleans the sewage before it is discharged to a source-water reservoir. As a general matter, construction of a sewer system involves the interconnection of some number of segments such as conduits (e.g., pipes), connectors, and the like, which cooperate with and take advantage of the natural effect of gravity to enable the desired sewage transfer to take place.

In the design, construction, and maintenance of a water management system, one important engineering metric or consideration is the determination of how much (i.e., the maximum amount) fluid the system (and/or a given segment of the system) is handling as well as its overall capacity (i.e., the amount that may pass through the system without giving rise to trouble conditions such as overflow, backup, and the like). This metric is often expressed as a "flow rate," which is the volume of waste water that passes through a given part of a waste water pipe per unit time (e.g., $ft^3/sec$ or $m^3/sec$).

SUMMARY

Obtaining direct measurements of flow rates may be cost prohibitive. The instruments required to measure flow rates may be expensive to purchase, install, or maintain. A less expensive option is to estimate flow rates of sewage and/or wastewater (hereinafter generally referred to as "sewage") based on other measurements that are less expensive to obtain. For example, using the "Gauckler-Manning-Strickler formula" (or simply the "Manning formula"), flow rates can be estimated based on characteristics of the sewage flow and the sewer pipe. Most variables of the Manning formula correspond to characteristics of the sewage and sewer pipe that are relatively static. Generally, just one variable of the Manning formula corresponds to a characteristic that changes within a relatively short period of time: the depth of the sewage. Advantageously, the depth of the sewage can be obtained with relatively inexpensive instruments (compared to those used to directly measure flow rates).

However, even relatively static characteristics of a sewer pipe may change over time. For example, environmental changes such as ground settling might alter the slope or shape of the sewer pipe, thus affecting the estimated-flow-rate calculations. The Manning formula is sensitive to the accuracy of the formula's variable values: even small errors in these values may affect the accuracy of the estimations produced by the formula. Accordingly, the variable values corresponding to these otherwise relatively static characteristics may need to be altered in order for the Manning formula to produce accurate flow-rate estimations.

However, like the direct measurements of flow rates, real-time measurements of these relatively static characteristics of the sewer pipe may be costly to obtain, especially after the sewer system has been constructed. Accordingly, when applying the Manning formula to estimate flow rates, the variable values corresponding to these characteristics may be based on estimates (perhaps such as historical values of these variables). Determining appropriate values for these variables in the abstract may be difficult without a way to quickly and easily understand how changes to these values will affect the flow-rate estimations. Each variable may affect the estimated flow rates in respectively different ways. It may be be advantageous to visualize how changing any one or more of these values would affect the estimated flow rates.

Described below are various embodiments that, inter alia, may be used to provide a visual (or other) representation of the estimated flow rates resulting from a modification of any of the values of the Manning formula variables. In one embodiment, a flow-estimation processor receives one or more flow-depth measurements with each flow-depth measurement having been taken at a respective time. The processor calculates a respective estimated flow rate for each of the one or more times such that each respective estimated flow rate is calculated based on at least (i) the corresponding flow-depth measurement and (ii) a set of one or more flow-estimation parameters each set to a respective initial value. The processor outputs the estimated flow rates for presentation via a user interface, and receives via the user interface one or more updated values, with each received updated value corresponding to a respective one of the flow-estimation parameters. The processor calculates an updated estimated flow rate for each of the one or more times, such that each respective updated estimated flow rate is calculated based on at least (i) the corresponding flow-depth measurement, (ii) the one or more received updated values, and (iii) respective initial values of any flow-estimation parameters for which no updated value was received. The processor then outputs the updated estimated flow rates for presentation via the user interface. The set of flow-estimation parameters could include one or more variables of the Manning formula and/or an offset of one or more of the flow-depth measurements, among numerous other possibilities.

These as well as other aspects, advantages, and alternatives will become apparent to those of ordinary skill in the art by reading the following detailed description, with reference where appropriate to the accompanying drawings. Further, it should be understood that the descriptions provided in this overview and below are intended by way of example and not limitation.

BRIEF DESCRIPTION OF THE FIGURES

Various exemplary embodiments are described herein with reference to the following drawings, in which like numerals denote like entities, and in which.

DETAILED DESCRIPTION OF THE FIGURES

The present systems and methods will now be described with reference to the figures. It should be understood, however, that numerous variations from the depicted arrangements and functions are possible while remaining within the scope and spirit of the claims. For instance, one or more elements may be added, removed, combined, distributed, substituted, re-positioned, re-ordered, and/or otherwise changed. Further, where this description refers to one or more functions being implemented on and/or by one or more devices, one or more machines, and/or one or more networks, it should be understood that one or more of such entities could carry out one or more of such functions by themselves or in cooperation, and may do so by application of any suitable combination of hardware, firmware, and/or software. For instance, one or more processors may execute one or more sets of programming instructions as at least part of carrying out of one or more of the functions described herein. Further, though the following disclosure makes references to sewage, sewer pipes, and sewage systems, it should be understood that the embodiments described herein may apply equally to any fluid in any conduit.

I. Exemplary Network Architecture

Figure 1:
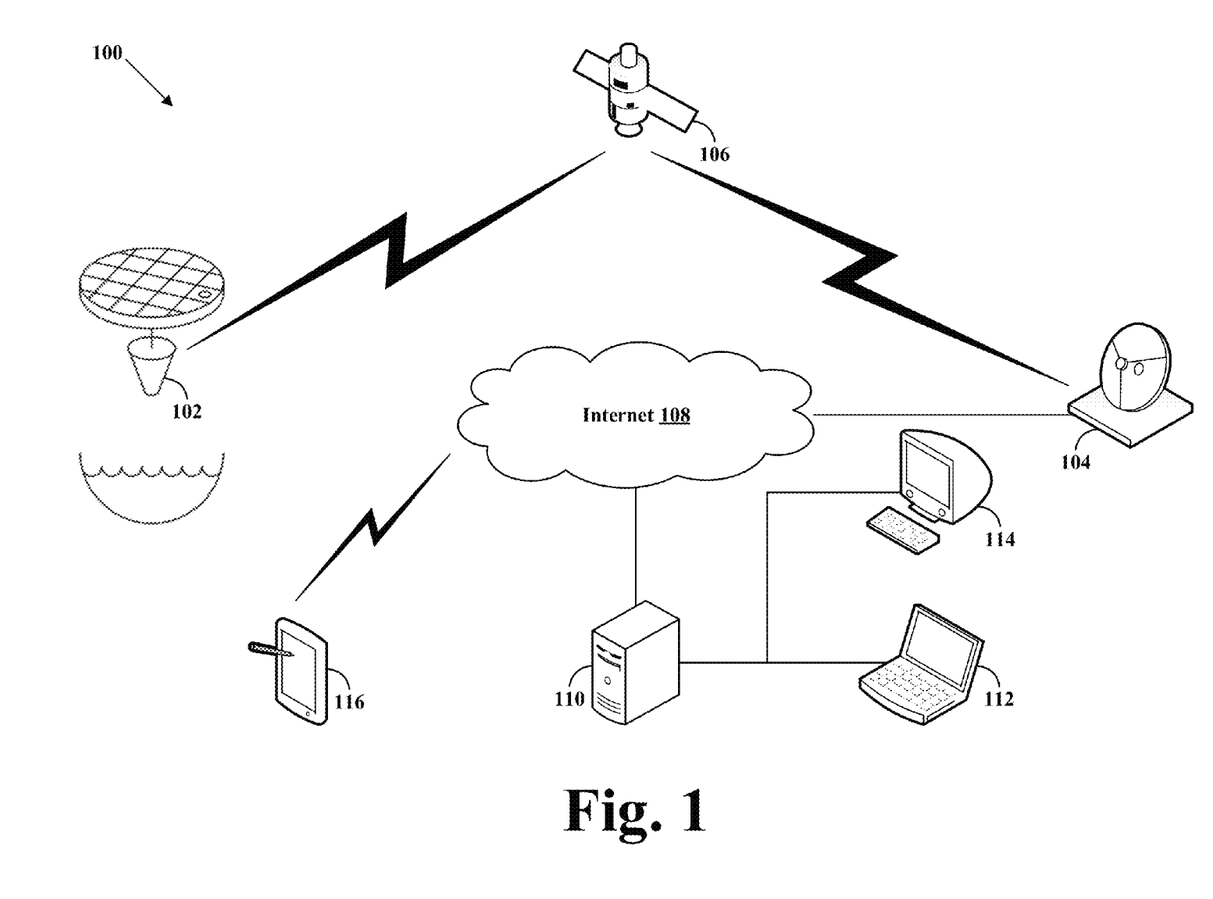
FIG. 1 is a diagram of a network, in accordance with exemplary embodiments.

FIG. 1 is a diagram of a network, in accordance with exemplary embodiments. As shown in FIG. 1, network 100 includes flow-depth sensor 102, base station 104, relay device 106, the Internet 108, server 110, local area network (LAN) computers 112 and 114, and remote computer 116, each of which are communicatively connected via one or more communication links. Network 100 may be generally configured to relay flow-depth measurements and other data between flow-depth sensor 102, server 110, and computers 112, 114, and 116 via one or more of the communication links. Other components such as routers, switches, repeaters, firewalls, and modems (among other possibilities) may be present as well. Those components may be interposed on the communication links between the flow-depth sensor, server, and computers, as examples. Those having skill in the art will understand that additional and/or different entities may be present in network 100, and that not all entities depicted in FIG. 1 are required to be present in network 100.

Flow-depth sensor 102 could be any component capable of performing the depth-sensor functions described herein. The flow-depth sensor may incorporate various components such as a power supply, a flow-depth measurement interface, and a wireless-communication interface for carrying out the depth-sensor functions. In an embodiment, the flow-depth sensor takes the form of a manhole cover that incorporates the various components, each of which are communicatively linked, incorporated within, and/or attached to the exterior of the manhole cover, as examples. Additional and/or different components could be included as part of the flow-depth sensor, and not all described components are required to be part of the flow-depth sensor. The sensor could take other forms as well, such as those described in U.S. Pat. No. 7,944,352, the entire contents of which are hereby incorporated by reference.

Base station 104 could be any component capable of performing the base-station functions described herein, and could take the form of a Wi-Fi router, a cellular base station, a network router or switch, and/or a satellite dish, among numerous other possibilities. Relay device 106 could be any component capable of performing the relay functions described herein. The relay device could take the form of a satellite, a femtocell, a Wi-Fi extender, a network router or switch, and/or an optical communications repeater, among many other examples. The Internet 108 could take the form of the eponymous wide area network (WAN), and/or could take the form of any other network. Those having skill in the art will understand that base station 104, relay device 106, and/or Internet 108 may take other forms as well.

Server 110 could be any device capable of carrying out the server functions described herein. As such, the server could take the form of one or more hardware servers that individually or collectively function as database servers, file servers, mail servers, web server, or application servers, among many other possibilities.

Computers 112, 114, and 116 could be any devices capable of carrying out the computer functions described herein, and could take the form of a general-purpose computer, a tablet, and/or a smartphone, among other possibilities. As described above, some computers (such as computers 112 and 114) may be connected to server 110 via a LAN. Other computers, such as computer 116, could be connected to server 110 via a WAN, such as the Internet 108. The computers could be communicatively linked to server 110 in other ways as well. As another possibility, the computers and server 110 could take the form of a single device. The computers could take other forms as well.

II. Exemplary Computing Entity

Figure 2:
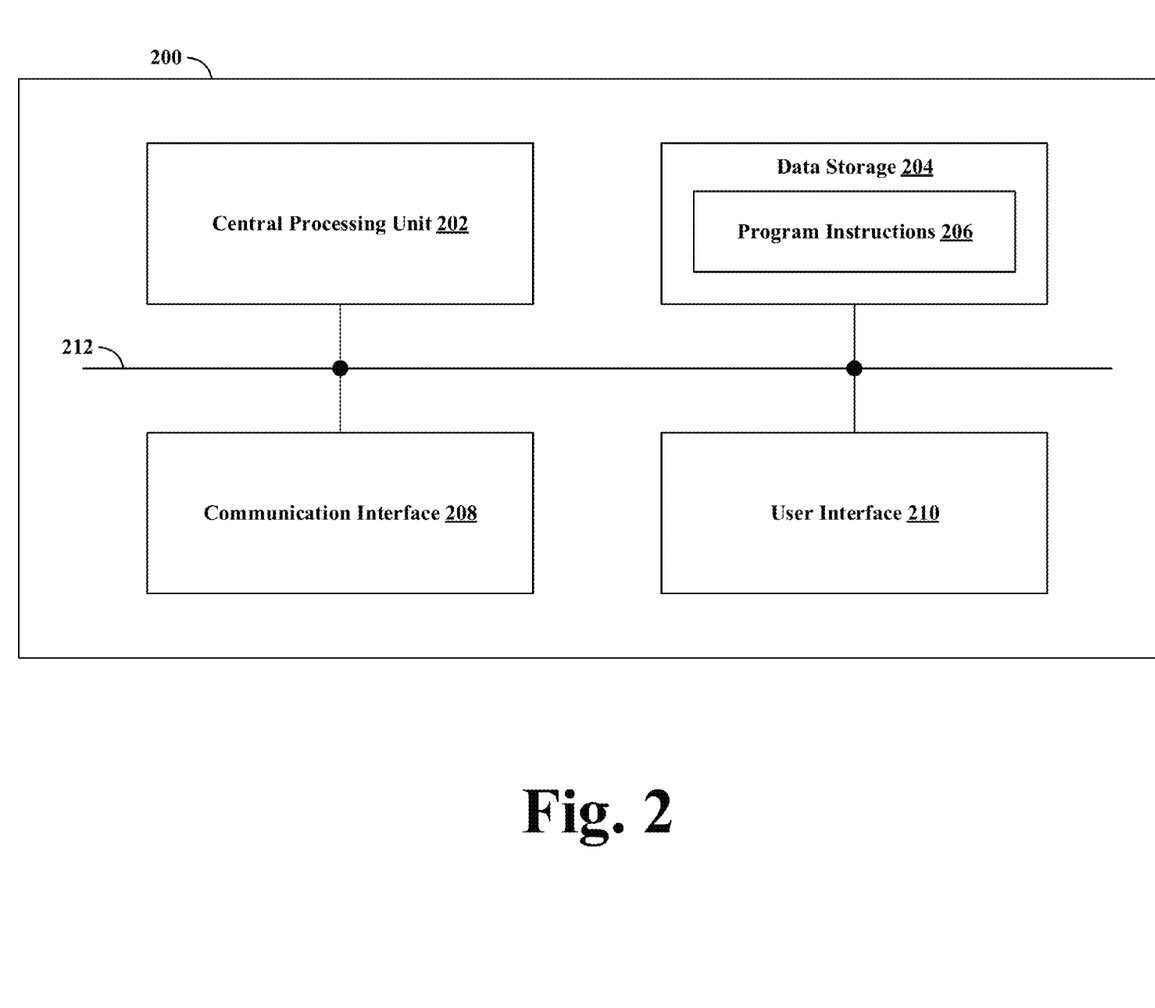
FIG. 2 is a simplified block diagram of a computing entity, in accordance with exemplary embodiments.

FIG. 2 is a simplified block diagram of a computing entity, in accordance with exemplary embodiments. Any one or more of the aforementioned flow-depth sensor 102, base station 104, relay device 106, Internet 108, server 110, and computers 112, 114, 116 could take the form of the following computer entity.

As shown in FIG. 2, computing entity 200 may include a central processing unit (CPU) 202, a data storage 204 containing program instructions 206, a communication interface 208, and a user interface 210, each of which are interconnected via a system bus 212. CPU 202 may take the form of one or more general-purpose processors and/or one or more special-purpose processors, and may be integrated in whole or in part with data storage 204, user interface 208, and/or communication interface 210. Data storage 204 may store program instructions 206, flow-depth measurements, flow-level measurement, and user-interface data, among numerous other possibilities. The data storage may take the form of a non-transitory computer-readable medium such as a hard drive, a solid-state drive, an EPROM, a USB storage device, a CD-ROM disk, a DVD disk, a relational database management system (RDBMS), any other non-volatile storage, or any combination of these, to name just a few examples. Program instructions 206 may comprise machine-language instructions executable by processor 204 to carry out various functions described herein.

User interface 208 may be any component capable of carrying out the user-interface functions described herein. The user interface may be configured to both receive input from a user and output information to the user. User input might be achieved via a keyboard, a mouse, or another component communicatively linked to a general-purpose computer. As another possibility, input may be realized via a touchscreen display of a smartphone or tablet device. Output may be provided via a computer monitor or a loudspeaker (such as a computer speaker), again possibly communicatively linked to a general-purpose computer. And some components may provide for both input and output, such as the aforementioned touchscreen display. Those having skill in the art will understand that user interface 210 may take numerous other forms as well.

Communication interface 210 may be any component capable of performing the communication-interface functions described herein. As such, the communication interface could include or take the form of an Ethernet, Wi-Fi, Bluetooth, and/or universal serial bus (USB) interface, among many other possibilities.

Figure 3:
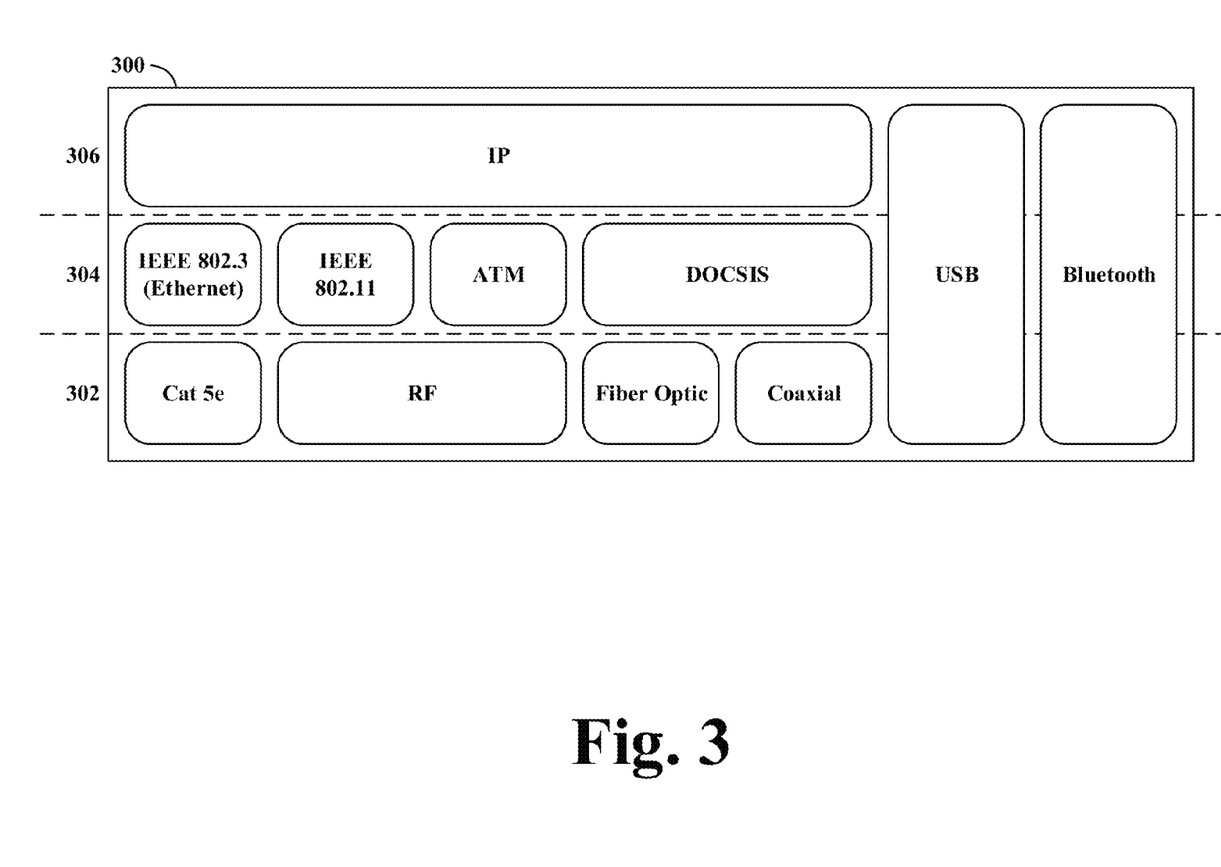
FIG. 3 is a diagram of a protocol stack of a communication interface, in accordance with exemplary embodiments.

FIG. 3 is a diagram of a protocol stack of a communication interface (such as communication interface 210). As shown in FIG. 3, protocol stack 300 may include a physical layer 302, a data link layer 304, a network layer 306, and an application layer 308. The protocol stack may include different and/or additional layers as well, and not all layers depicted in FIG. 3 are required for the protocol stack. Moreover, though layers 302, 304, and 306 are described as a physical layer, a data link layer, and a network layer, respectively, those having skill in the art will understand that the various interfaces and protocols described as part of these layers could actually exist in one or more different layers. Some interfaces and/or protocols might span more than one layer: for example, both the Bluetooth and USB specifications define at least a physical layer and a data link layer.

As shown in FIG. 3, physical layer 302 may take the form of an Ethernet over twisted pair interface, a radio frequency (RF) interface, a fiber-optic interface, a coaxial interface, a USB interface, and/or a Bluetooth® interface. The physical layer could also take the form of an IEEE 1394 (FireWire®) interface, a digital video interface (DVI), a video graphics array (VGA), a DisplayPort interface, a ThunderBolt interface, a peripheral component interconnect (PCI) or PCI Express (PCIe) interface, or any combination of these. Those having skill in the art will recognize that the physical layer of communication interface 210 may take other forms as well.

Data link layer 304 could take the form of one or more datagrams transmitted over physical layer 302 in compliance with one or more protocols, as just one possibility. Examples of such protocols include 802.3 (Ethernet), 802.11 (Wi-Fi), asynchronous transfer mode (ATM), and data over cable service interface specification (DOCSIS), among numerous other examples. Some data-link-layer protocols may be generally carried over a given physical-layer interface: for example, Wi-Fi may be generally carried over an RF interface, and DOCSIS over a hybrid fiber-coaxial interface. It should be understood, however, that a given physical-layer interface may carry data in a variety of data-link-layer protocols, and that a given data-link-layer protocol may carry data over a variety of physical-layer interfaces: for example, Ethernet datagrams may be carried over a twisted pair interface or a coaxial interface. Data link layer 304 could take other forms as well.

In an embodiment, network layer 306 takes the form of one or more packets carried over data link layer 304. The packets could conform to the Internet Protocol (IP), which includes Internet Protocol Version 4 (IPv4) and Internet Protocol Version 6 (IPv6). The network layer could take other forms.

A given protocol-stack layers may be configured to communicate data over a respective geographic area. For example, an Ethernet over Twisted Pair interface carrying data over a Category 5e cable may be able to carry data over a maximum distance of 100 meters. Several communicatively linked Ethernet interfaces may be able to exchange Ethernet frames over a Local Area Network (LAN) to a cable modem, which may then convert the Ethernet frames to DOCSIS for transmission to a local cable-internet provider. And a combination of several Ethernet and DOCSIS links might carry one or more IP packets over the worldwide Internet 108.

It should be understood that a given communication may be carried in a variety of different forms within any given protocol-stack layer. For example, a communication may be transmitted from a cable-internet provider initially over a fiber-optic interface to a neighborhood substation, and may be converted at the substation to a coaxial interface for delivery to an end user.

Those having skill in the art will understand that protocol stack 300 may include additional and/or different layers, and that not all layers shown in FIG. 3 need be included in the protocol stack. Further, one or more of the layers could be combined into a single layer, and/or a single layer could be separated into two layers. Other modifications are possible as well.

III. Exemplary Flow-Depth Measurement

Figure 4:
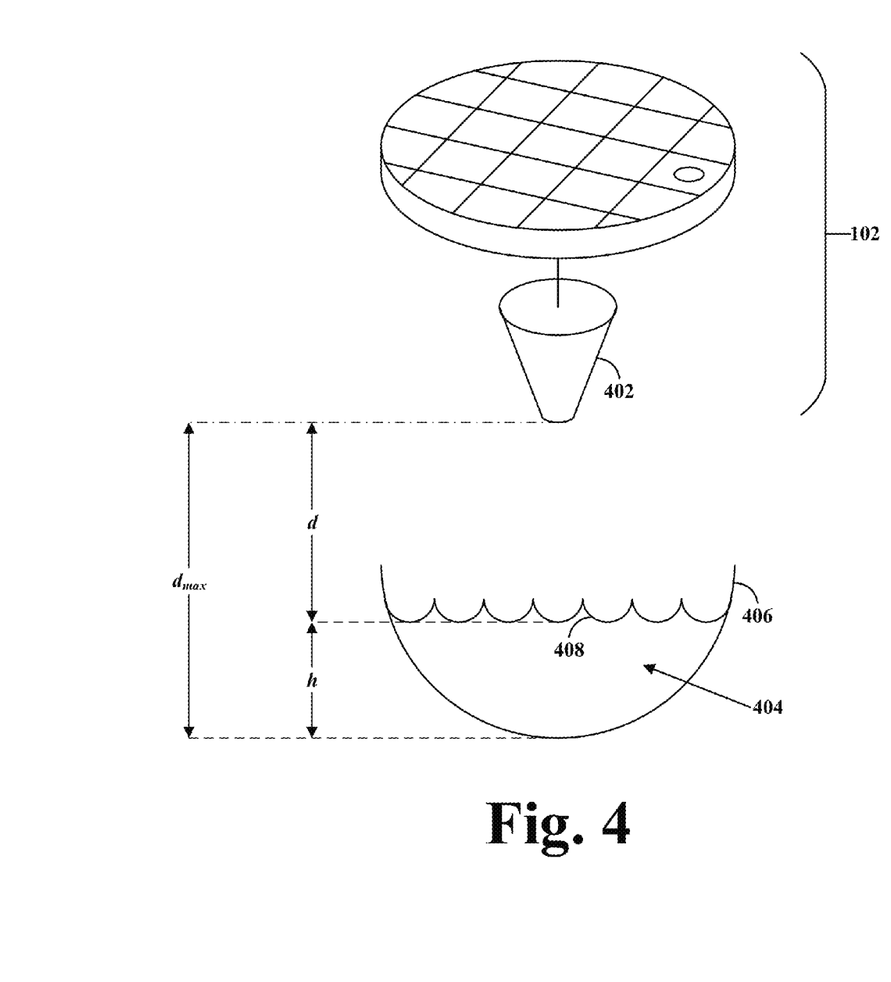
FIGS. 4, 5a, and 5b are illustrations of the various components of a flow-depth measurement, in accordance with exemplary embodiments.
Figure 5A:
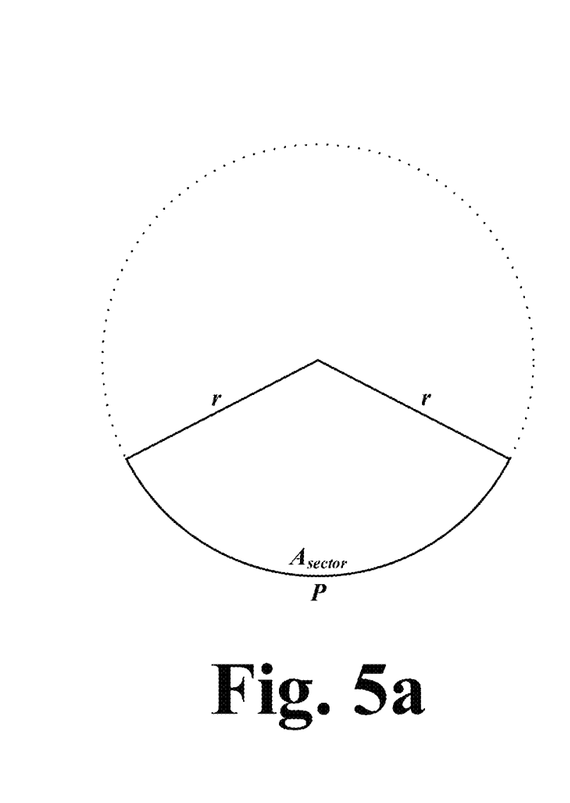
Figure 5B:
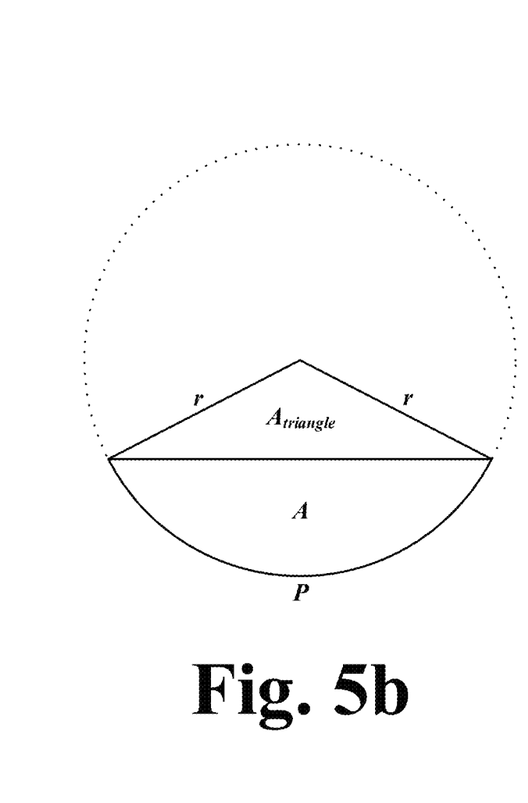

FIGS. 4, 5a, and 5b illustrate the various components of a flow-depth measurement. As shown in FIG. 4, a flow-depth sensor 102 is disposed over a sewer pipe (or other conduit) 406 capable of storing and/or transporting sewage (or other fluid) 404. Flow-depth measurement instrument 402 may be configured to measure a distance from the instrument to a surface of a remote object, such as distance d to free surface 408 of fluid 404 or a distance $d_{max}$ to a deepest-point of conduit 406. As another possibility, the flow-depth sensor could float on free surface 408, and/or could be attached to a surface of conduit 406. Those having skill in the art will recognize that the flow-depth measurement instrument may able to obtain distances d and $d_{max}$ from other positions as well.

Measurements of distances d and $d_{max}$ might be obtained via one or more measurement technologies. For example, the measurements might be optical measurements, perhaps made via one or more of a CMOS or CCD image sensor. As another possibility, the measurements might be one or more of a radar measurement, a sonar measurement, and an ultrasound measurement. Other distance-measuring technologies might also be used in addition to or instead of these previously-mentioned technologies. Further, a measurement of distance $d_{max}$ to conduit surface 406 might be obtainable only while no fluid is present in conduit 406. If sewage is present in conduit 406, $d_{max}$ might be obtained based on schematics of the conduit.

The flow depth h of sewage 404 can be calculated by subtracting distance d to free surface 408 from distance $d_{max}$ to conduit surface 406. Either or both of sensor 102, server 110, and computers 112, 114, and 116 could calculate depth h. For example, server 110 could receive both distances d and $d_{max}$ from sensor 102 and calculate depth h based on these distances, or the server could receive only distance d and calculate depth h based on a previously-stored distance $d_{max}$. Further still, server 110 could receive depth h calculated by sensor 102.

Having obtained flow depth h of sewage 404, Manning's formula can be used to estimate the flow rate of the sewage. The formula is $$Q = VA = \left(\frac{k}{n}\right)AR^{\frac{2}{3}}\sqrt{S}$$

where Q is the volumetric flow rate (m³/s), V is the mean velocity (m/s), A is the cross-sectional area of flow (m²), n is Manning's coefficient of roughness, R is the hydraulic radius (defined as the flow area divided by the wetted perimeter), and S is the slope of the of the conduit. The constant k is a conversion factor: the parameters are SI units of measure if k=1, while the parameters are statutory measurements if k=1.49.

The cross-sectional area A and the hydraulic radius R of conduit 406 can be obtained as a function of a flow depth h using the following equation if the conduit is circular $$A = A_{sector} - A_{isosceles\ triangle} = r^2\cos^{-1}\frac{(r-h)}{r} - (r-h)\sqrt{2rh - h^{\wedge}2}$$

where r is the radius of the conduit. FIG. 5a illustrates the area $A_{sector}$ of the circular sector defined by the wetted perimeter P of fluid 404, and FIG. 5b illustrates the area $A_{isosceles\ triangle}$ of the isosceles triangle extending from flow surface 408 to the cross-section center of conduit 406. The area A can be obtained by subtracting the area $A_{isosceles\ triangle}$ of the isosceles triangle from the area $A_{sector}$ of the sector.

The hydraulic radius R of conduit can be obtained using $$R = \frac{\pi r^2}{2\pi r} = \frac{r}{2}$$

where r is again the cross-sectional radius of the conduit.

Since A and R can be obtained as functions of pipe radius r and flow depth h, the flow rate Q of sewage 404 can be obtained using only the slope, the roughness coefficient, the cross-sectional radius of conduit 410, and depth h.

IV. Exemplary Operation

Figure 6:
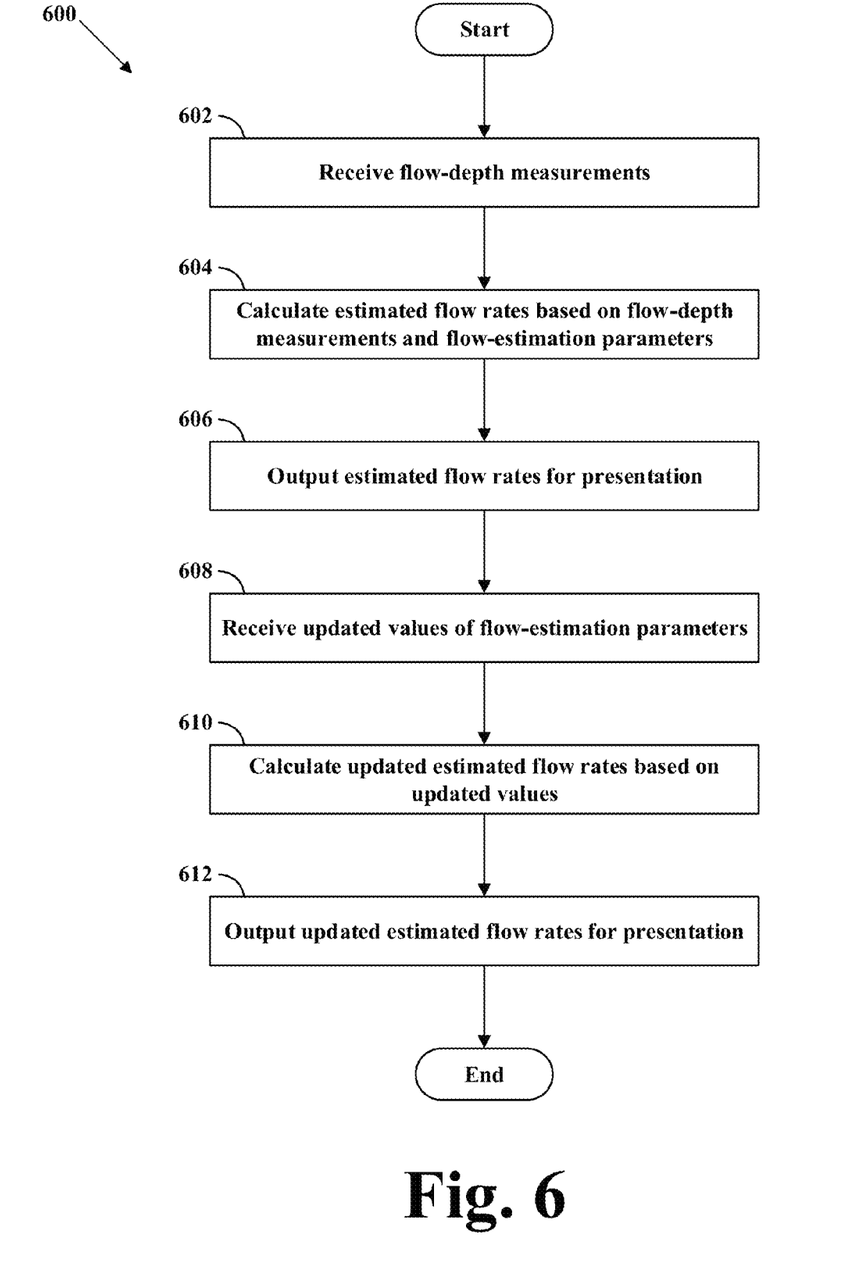
FIGS. 6, 9, and 11 are flowcharts of respective methods, in accordance with exemplary embodiments.

FIG. 6 is a flowchart of a method of estimating flow rates of a liquid in a conduit and outputting the estimated flow rates for presentation via a user interface. The method is described below as being carried out by a flow-estimation processor, which could take the form of flow-depth sensor 102, server 110, computers 112, 114, and/or 116, any other entity capable of performing the flow-estimation-processor functions described below, or any combination of these. In an embodiment, the flow-estimation processor takes the form of server 110, which performs the various flow-estimation-processor functions. In another embodiment, the flow-estimation processor takes the form of a system that includes both server 110 and flow-depth sensor 102: flow-depth sensor 102 performs various functions (such as calculating a flow depth and/or an estimated flow rate, for example), and server 110 performs other functions (e.g., outputting the flow depth and/or estimated flow rate for presentation and/or providing an interface for a user to input new model parameter values, which may then be communicated to the flow rate sensor). Those having skill in the art will understand that the flow-estimation processor could take other forms as well without departing from the scope of the claims.

As shown in FIG. 6, method 600 begins at step 602 with the flow-estimation processor receiving one or more flow-depth measurements, each flow-depth measurement having been taken at a respective time. In an embodiment, the flow-depth measurements are received from flow-depth sensor 102, though the flow-depth measurements might be received from other entities as well, such as a database server communicatively linked to the flow-estimation processor via server 110, Method 600 continues at step 604 with the flow-estimation processor calculating a respective estimated flow rate for each of the one or more times. Each respective estimated flow rate is calculated based on at least (i) the corresponding flow-depth measurement and (ii) a set of one or more flow-estimation parameters each set to a respective initial value.

The set of one or more flow-estimation parameters could include one or more variables of the Manning formula described above, or could include all of the variables of the Manning formula. As another possibility, the set of one or more flow-estimation parameters could include a flow-depth-measurement offset by which one or more of the flow-depth measurements are be offset. For example, a set of flow-depth measurements {1 ft, 3 ft, 4 ft, 4 ft, 3 ft, 2 ft, 1 ft} might be offset by a value of +1, resulting in a set of offset flow-depth measurements {2 ft, 4 ft, 5 ft, 5 ft, 4 ft, 3 ft, 2 ft}. As another example, the set of flow-depth measurements might be offset by a value of −2, resulting in a set of offset flow-depth measurements {0 ft, 2 ft, 3 ft, 3 ft, 2 ft, 1 ft, 0 ft}. The offset flow-depth measurements might then be used as parameters in calculating the estimated flow rates. As another possibility, the set of one or more flow-estimation parameters could include any one or more flow-depth-measurement offsets and/or variables of the Manning formula.

Figure 7:
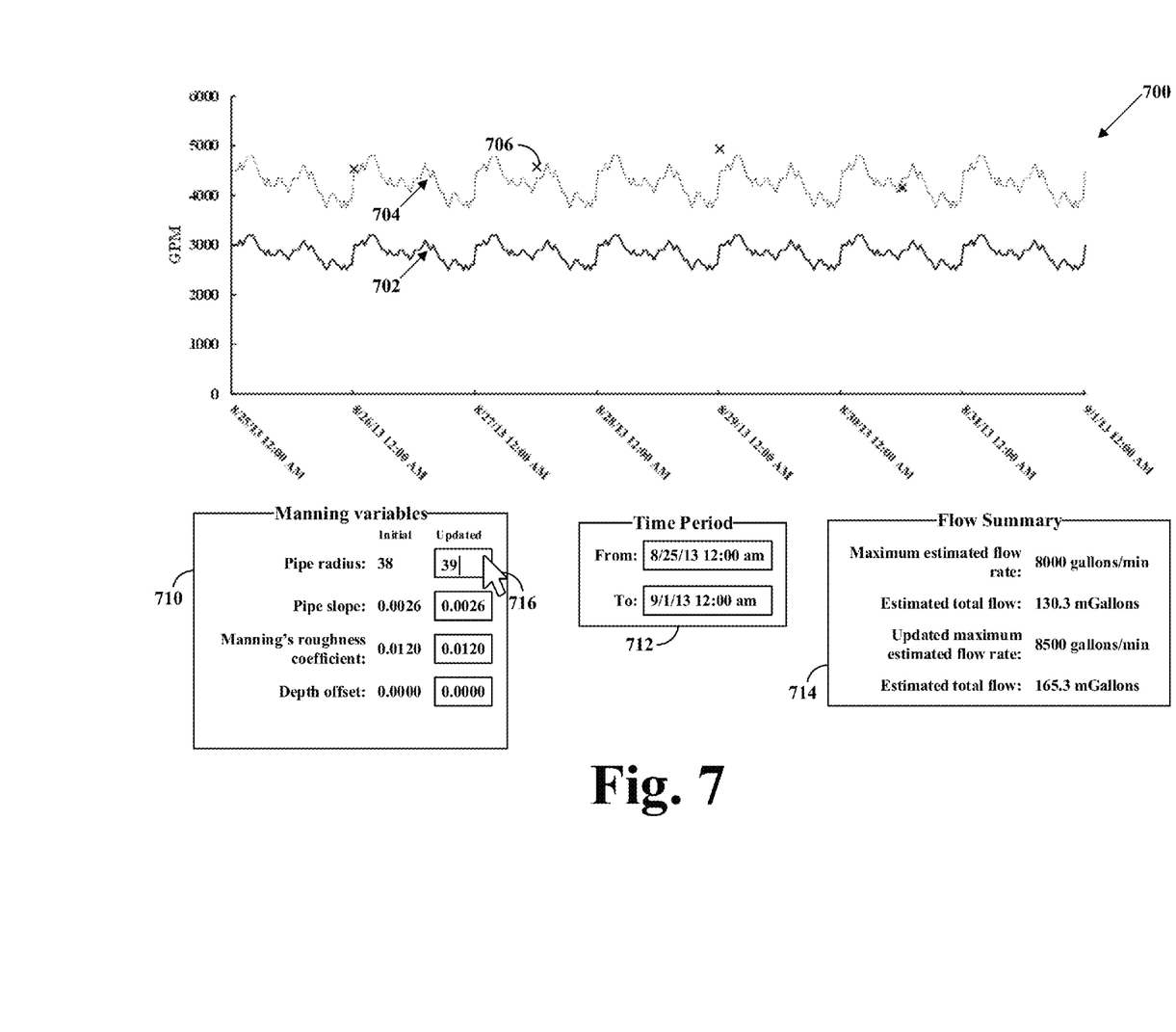
FIGS. 7 and 10 are illustrations of respective user interfaces, in accordance with exemplary embodiments.

FIG. 7 is an illustration of a user interface, in accordance with exemplary embodiments. According to an embodiment illustrated in FIG. 7, a flow-estimation processor outputs initial values of one or more of the flow-estimation parameters for presentation via user interface 700. User interface 700 includes, among other elements, UI box 710 displaying "initial" values for several flow-estimation parameters corresponding to respective variables of the Manning formula. The displayed parameters include a pipe radius, a pipe slope, a Manning roughness coefficient, and a depth offset. Those having skill in the art will understand that additional and/or different flow-estimation parameters may output for presentation, and that the initial values of the flow-estimation parameters may be presented in various other ways.

Method 600 continues at step 606 with the flow-estimation processor outputting the estimated flow rates for presentation via user interface 210. In an embodiment, presentation of the estimated flow rates comprises presentation of a graph of the flow rates over a period of time. In another embodiment, presentation of the estimated flow rates comprises presentation of a list of the flow rates and the respective time. In a further embodiment, presentation of the estimated flow rates comprises presentation of a total flow over a period of time.

According to an embodiment illustrated in FIG. 7, presentation of the estimated flow rates takes the form of a graph of the flow rates over a period of time. Solid line 702 represents the estimated flow rates and dashed line 704 represents the updated estimated flow rates (discussed blow). UI box 712 may be used to specify the time period over which the estimated flow rates are presented; as shown in FIG. 7, the presented estimated flow rates span the week of August 25 to August 31 (and ending at midnight of September 1). The horizontal axis could represent minutes, hours, days, and/or any other period of time. The vertical axis could be in units of gallons/minute, $ft^3$/sec, $m^3$/sec, or any other units of volumetric flow. Those having skill in the art will recognize that the graph may take other forms as well.

In an embodiment, the flow-estimation processor may output for presentation a maximum estimated flow rate over a period of time. The maximum estimated flow rate could be indicated by a dot or vertical line on user interface 700. As another possibility, the maximum flow rate could be indicated by text on a display, e.g., "Maximum flow rate: 50 $m^3$/sec). Those having skill in the art will recognize that the maximum estimated flow rate may be indicated in other ways as well. Further, other metrics such as a minimum, mean, and/or median estimated flow rate over a period of time may be output for presentation as well. The flow-estimation processor may first calculate the maximum, minimum, mean, and/or median estimated flow rates before outputting them for presentation; additionally or alternatively, the flow-estimation processor may receive the calculations from another entity (such as flow-depth sensor 102, server 110, and/or computers 112, 114, and/or 116).

Method 600 continues at step 608 with the flow-estimation processor receiving one or more updated values via the user interface, with each received updated value corresponding to a respective one of the flow-estimation parameters. In an embodiment, the user interface presents an initial value of one or more of the estimated flow rates. The updated values might be obtained via manipulation of the presented initial values, perhaps by receiving typed input corresponding to the updated values (and overwriting the initial values), or by receiving mouse clicks corresponding to an increase or a decrease of a given one or more of the flow-estimation parameters. Those having skill in the art will understand that the values may be received in other ways as well.

According to an embodiment illustrated in FIG. 7, the updated values may be specified by typing a new value in a text box corresponding to a respective flow-estimation parameter. The text box may be chosen for text entry by placing mouse cursor 716 over the text box and pressing a button on a mouse or a key on a keyboard, as examples. The updated values may be received by the flow-estimation processor immediately upon entry of the values, and/or the updated values may be received subsequent to specification via the user interface that entry of updated values is complete. Those having skill in the art will recognize that the updates values may be specified in other ways as well.

In an embodiment, the flow-estimation processor may additionally receive one or more flow-rate measurements and output those measurements for presentation. For example, flow rates may be occasionally "spot checked" by measuring a flow rate at the location of a respective flow-depth sensor 102. These measured flow rates may be presented with the estimated flow rates to assist in choosing accurate values of the flow-estimation parameters. For example, as shown in FIG. 7, the one or more flow-rate measurements may be presented as checkmarks (such as checkmark 706) on a graph of the estimated flow rates. The placement of the checkmarks may indicate the date and time of the measurement as well as the measured flow rate. Those having skill in the art will recognize that presentation of the flow-rate measurements make take other forms as well.

Method 600 continues at step 610 with the flow-estimation processor calculating an updated estimated flow rate for each of the one or more times. Each respective updated estimated flow rate is calculated based on at least (i) the corresponding flow-depth measurement, (ii) the one or more received updated values, and (iii) respective initial values of any flow-estimation parameters for which no updated value was received. At step 612, the flow-estimation processor outputs the updated estimated flow rates for presentation via the user interface. Calculation and presentation of the updated estimated flow rates may take a form similar (or identical) to the calculation and presentation of the estimated flow rates. As shown in FIG. 7, the presentation of the updated estimated flow rates may take the form of a graph, with dashed line 706 representing the updated estimated flow rates.

Figure 8:
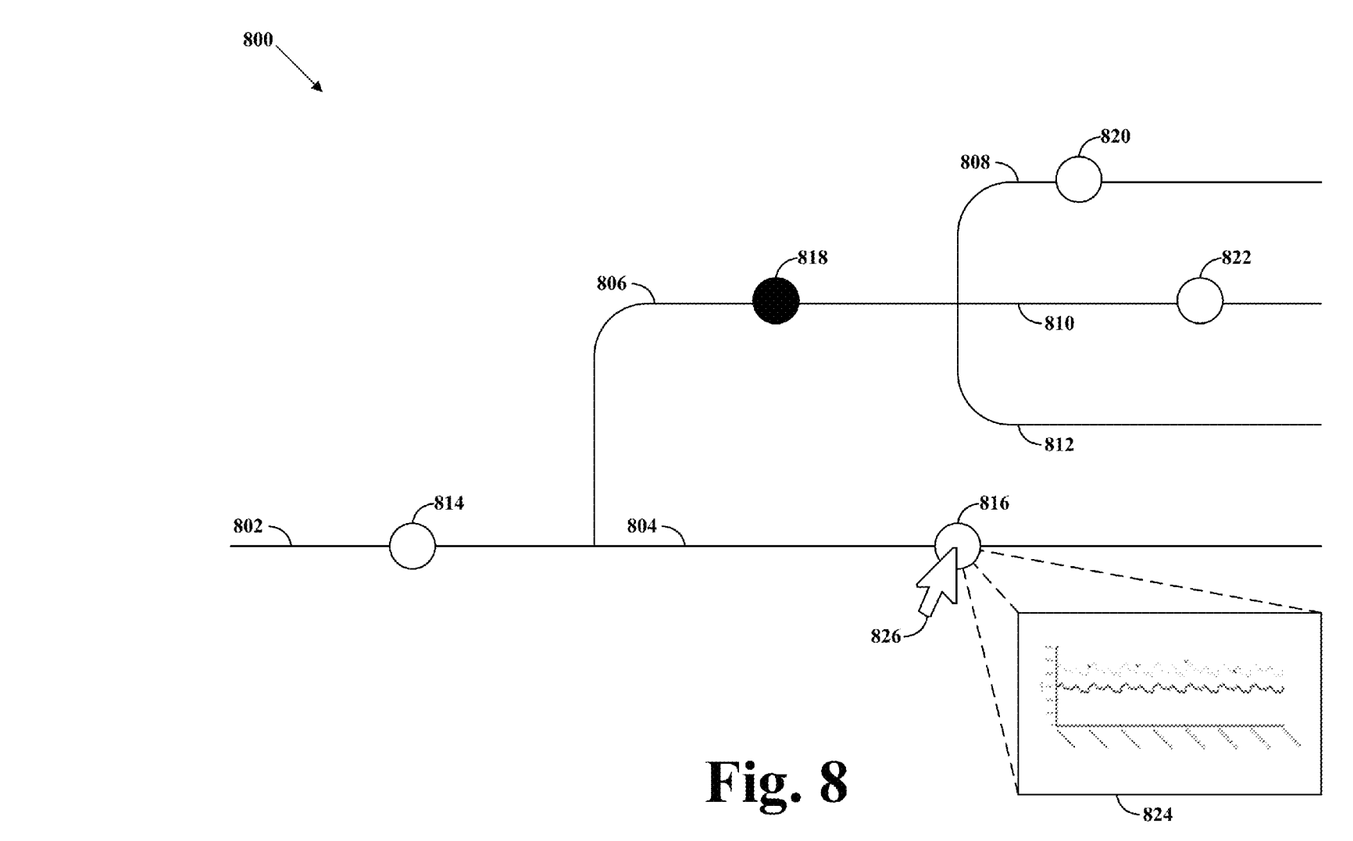
FIG. 8 is a simplified map of a system of conduits, in accordance with exemplary embodiments.

FIG. 8 is a simplified map of a system of conduits, in accordance with exemplary embodiments. As shown, system 800 includes conduit sections 802, 804, 806, 808, 810, and 812, some of which are branches of other conduit sections. Flow-depth sensors are disposed along several (though not necessarily all) conduit sections. For example, system 800 includes flow-depth sensors 814, 816, 818, 820, and 822 (indicated by hollow spheres) disposed along conduit sections 802, 804, 806, 808, and 810, respectively. Further, flow-depth sensor 818 also includes a flow-rate sensor for directly measuring flow rates.

Flow-rate and/or flow-depth information might be obtained by specifying a respective flow-depth sensor via a user interface. As illustrated in FIG. 8, for example, mouse pointer 826 might be used to select flow-depth sensor 816. In response to selection of the flow-depth sensor, the flow-estimation processor may present a graph of estimated flow rates and flow-rate measurements similar to the graph presented in FIG. 7.

Flow-rate and/or flow-depth information for a respective flow-depth sensor might be used to choose values for flow-estimation parameters for other conduit sections. For example, if the chosen values for flow-depth sensor 818 are accurate (based on a comparison of the estimated flow rates with the measured flow rates), then those same values might be used for flow-depth sensors 820 and 822. Those having skill in the art will recognize that the user-interface map may take other forms as well.

V. Second Exemplary Operation

The Manning formula provides accurate estimates of flow rates if certain conditions are true. First, the flow should be an open-channel flow, which has a free surface subject to atmospheric pressure and is only partially enclosed by a solid boundary. Flow in a closed conduit (enclosed by a solid boundary such as a sewer pipe) can be treated as an open-channel flow if the fluid has a free surface. Thus sewage can generally be treated as an open flow since it is usually only partially enclosed by a sewer pipe and generally has a free surface.

Further, for the Manning formula to provide accurate estimates of flow rates, the above-described open-channel flow should be a steady and uniform flow. A steady flow exists if characteristics of the flow (represented in the Manning formula) do not vary with time, while a uniform flow exists if those characteristics do not vary with distance. Thus a steady and uniform flow is possible only in conduits that have a constant cross section and slope.

However, while the Manning formula generally applies to open-channel steady and uniform flows, the formula can estimate flow rates of non-steady or non-uniform flows if the flows deviate from these constraints within a certain threshold.

Figure 9:
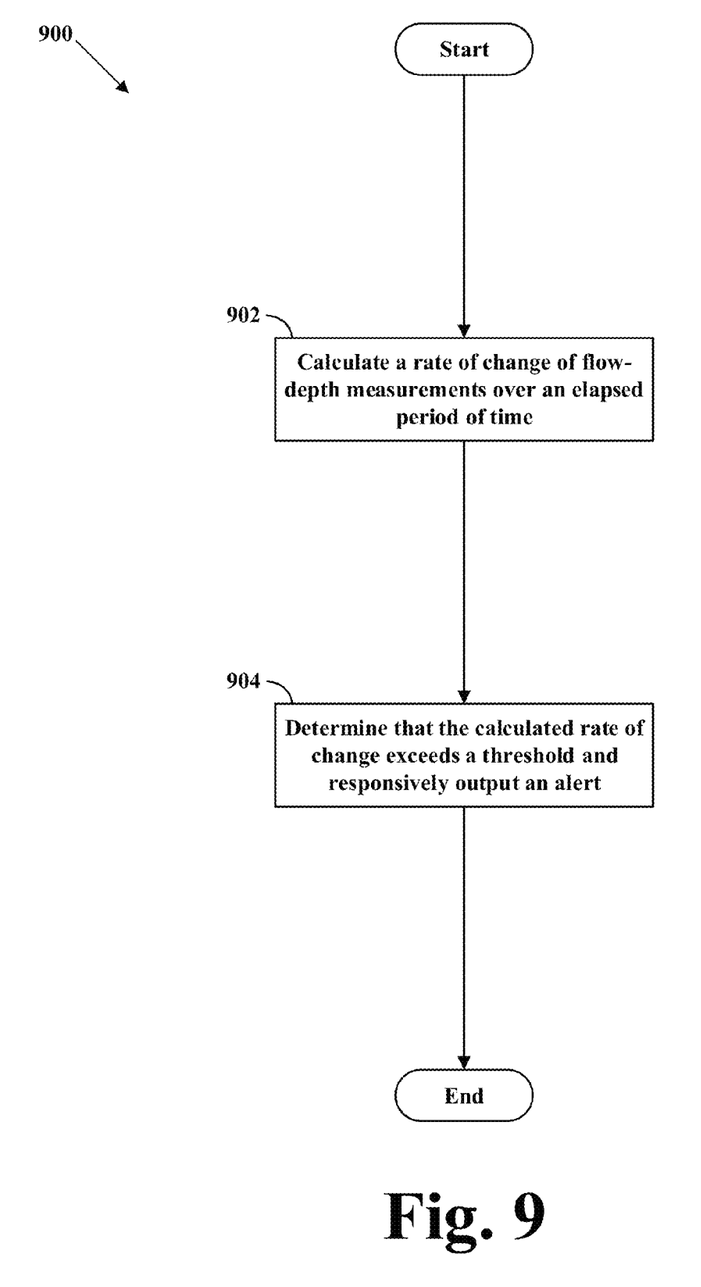

FIG. 9 is a flowchart of a method carried out by a flow-estimation processor, in accordance with exemplary embodiments. As shown, method 900 begins at step 902 with the flow-estimation processor calculating a rate of change of flow-depth measurements over an elapsed period of time. At step 904, the flow-estimation processor makes a rate-change determination that the calculated rate of change exceeds a rate-of-change threshold, and responsively outputting a rate-of-change alert via the user interface.

In an embodiment, calculating the rate of change includes calculating the standard deviation of the flow-depth measurements, and making the rate-change determination includes determining that the standard deviation exceeds a threshold. In another embodiment, the flow-estimation processor additionally calculates a rate of change over a second elapsed period of time within the first period of time, makes a second rate-change determination that the second calculated rate of change exceeds a second rate-of-change threshold, and responsively outputs the rate-of-change alert.

VI. Third Exemplary Embodiment

Figure 10:
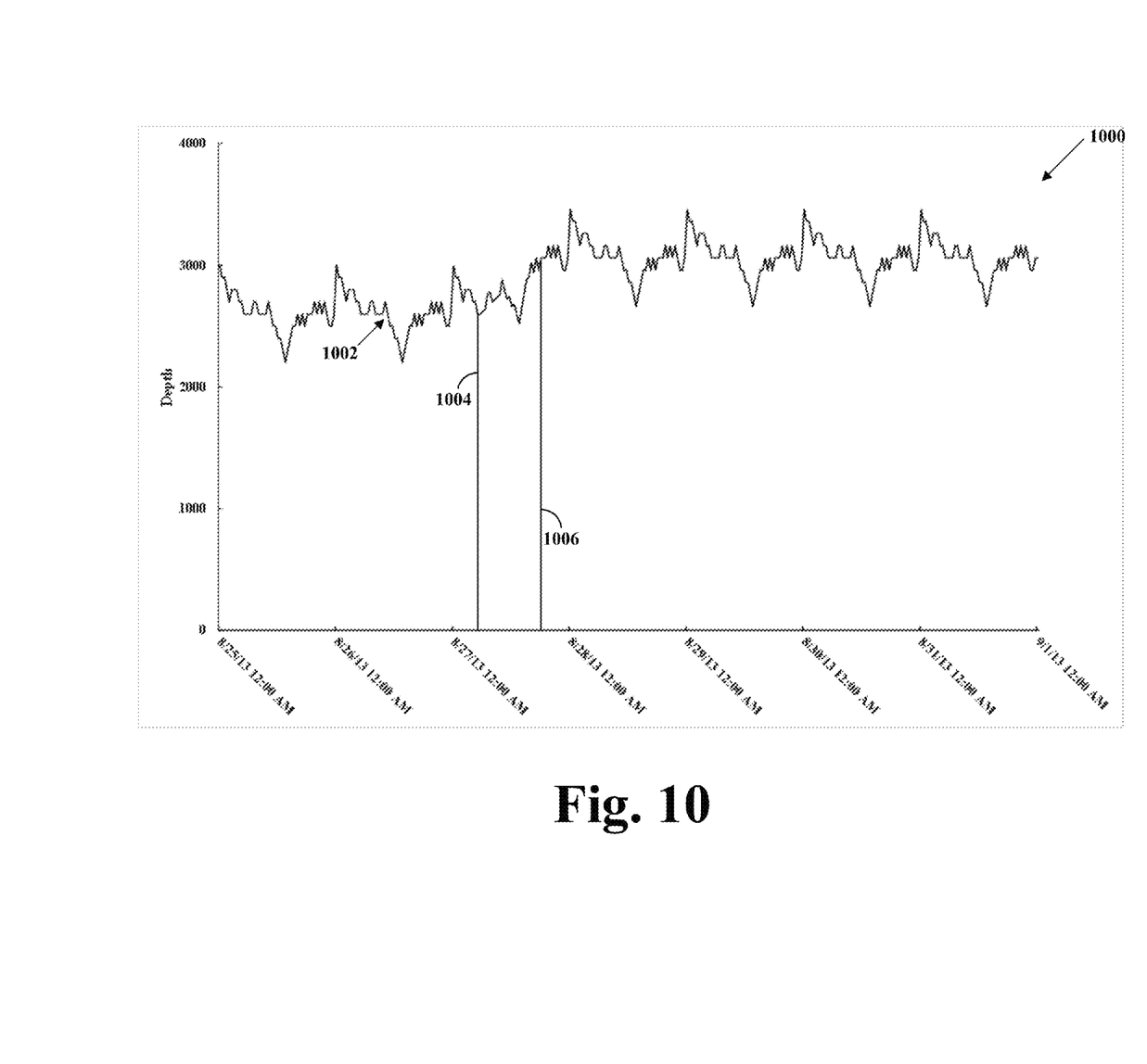

Accumulation of sediment over time within a sewer pipe may result in inaccurate flow-depth measurements. To illustrate, FIG. 10 depicts a graph of estimated flow-depth measurements 1002 over a length of time. The values of the flow-depth measurements are periodic—that is, the general flow-depth pattern repeats several times over the length of time. As shown however, the flow-depth measurements increase between periods 1004 and 1006 while the measurements in the other periods maintain their general flow-depth signature. This increase of the flow-depth measurements may be a result of accumulation of sediment in the sewer pipe, and the flow rates of the sewage may not have changed despite the change of the flow-depth signature. Thus the sediment accumulation may falsely indicate a change in the flow-rate signature when in fact there is no change.

Figure 11:
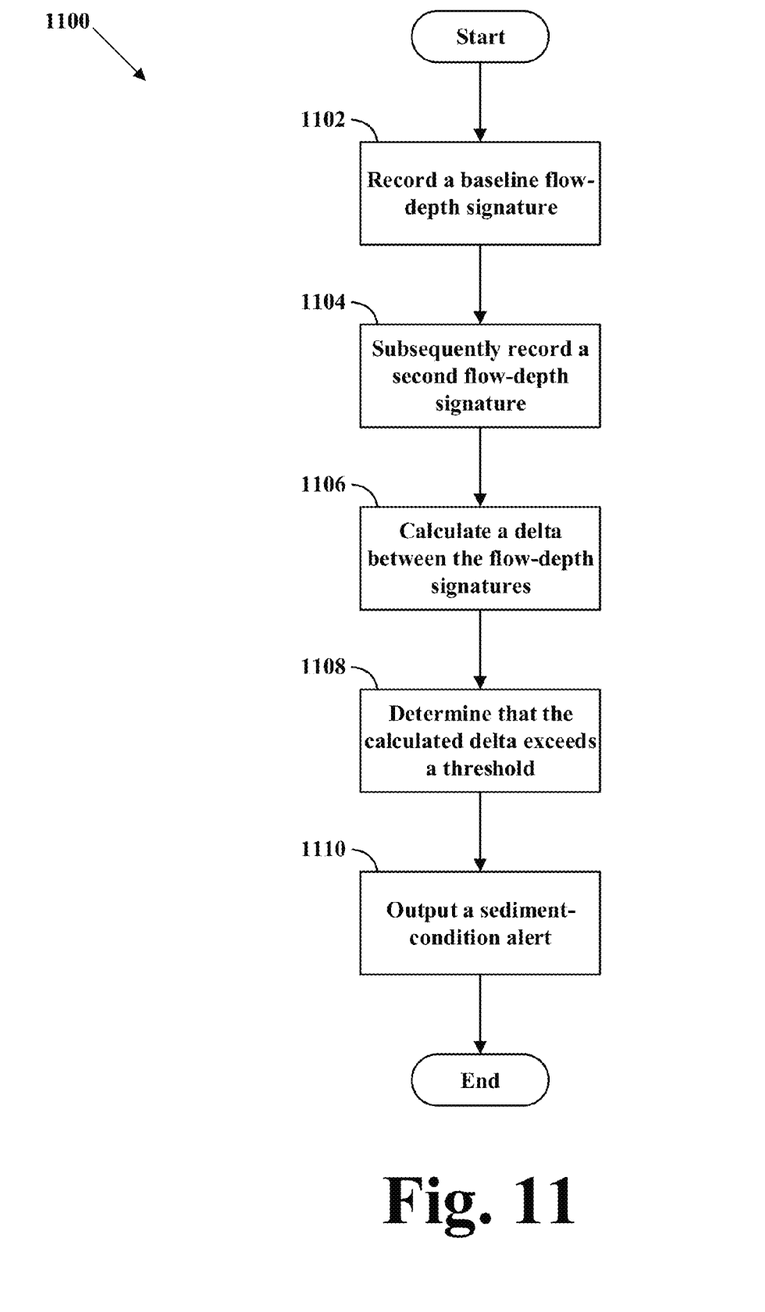

FIG. 11 is a flowchart of a method of detecting a sediment condition in a conduit and outputting a sediment-condition alert. The method is described as being carried out by a sediment-detection processor, which could take a form similar (or identical) to the above-described flow-estimation processor. The method could additionally or alternatively be carried out by other entities as well.

As shown, method 1000 begins at step 1102 with a sediment-detection processor recording a baseline flow-depth signature during a first time period. Recording the baseline flow-depth signature includes receiving and recording a first plurality of flow-depth measurements taken at different respective times during the first time period. Thus, for example, the first plurality of flow-depth measurements might correspond to a period during which it is known that no sediment has accumulated in the conduit.

At step 1104, the sediment-detection processor records a second flow-depth signature during a second time period subsequent to the first. Recording the second flow-depth signature includes receiving and recording a second plurality of flow-depth measurements taken at different respective times during the second time period. The second plurality of flow-depth measurements might correspond to a time period during which sediment has possibly accumulated in the conduit.

The method continues at step 1106 with the sediment-detection processor calculating a delta between the second flow-depth signature and the baseline flow-depth signature. Calculating the delta could include calculating a difference between the mean and/or median of the first and second pluralities of flow-depth measurements, though other techniques for calculating the delta are possible. At step 1108, the sediment-detection processor makes a sediment-condition determination that the calculated delta exceeds a delta threshold, and responsively outputs a sediment-condition alert for presentation via a user interface. The alert could take the form of a pop-up window, an email message, a short message service (SMS) message, a push notification, an audible alert, or any combination of these, among other possibilities. The alert could convey the value of the calculated delta, which might then be provided to the flow-estimation processor as the value for the flow-depth-offset parameter. The alert might include an indication that the flow-depth-offset parameter should be adjusted. And/or the alert could convey information such as (or relating to) the delta threshold, the first or second time period, the first or second plurality of flow-depth measurements, the baseline or second flow-depth signature, or any combination of these, as examples. The alert may or may not indicate that the calculated delta exceeds a delta threshold. Those having skill in the art will understand that the alert may take other forms as well.

VII. Conclusion

While some example embodiments have been described above, those of ordinary skill in the art will appreciate that numerous changes to the described embodiments could be made without departing from the scope and spirit of the claims.

The invention claimed is:

1. A method of estimating flow rates of a liquid in a conduit, the method comprising:
    a flow-estimation processor receiving one or more flow-depth measurements, each flow-depth measurement having been taken at a respective time;
    the flow-estimation processor calculating a respective estimated flow rate for each of the one or more times, wherein each respective estimated flow rate is calculated based on at least (i) the corresponding flow-depth measurement and (ii) a set of one or more flow-estimation parameters each set to a respective initial value;
    the flow-estimation processor outputting the estimated flow rates for presentation via a user interface;
    the flow-estimation processor receiving via the user interface one or more updated values, each received updated value corresponding to a respective one of the flow-estimation parameters;
    the flow-estimation processor calculating an updated estimated flow rate for each of the one or more times, wherein each respective updated estimated flow rate is calculated based on at least (i) the corresponding flow-depth measurement, (ii) the one or more received updated values, and (iii) respective initial values of any flow-estimation parameters for which no updated value was received; and
    the flow-estimation processor outputting the updated estimated flow rates for presentation via the user interface.

2. The method of claim 1, wherein at least one of the flow-depth measurements comprises a measurement selected from a group of measurements consisting of an optical flow-depth measurement and an ultrasound flow-depth measurement.

3. The method of claim 1, wherein the set of flow-estimation parameters comprises a flow-depth-measurement offset.

4. The method of claim 1, wherein the set of flow-estimation parameters comprises one or more of a conduit radius, a conduit slope, and a roughness coefficient.

5. The method of claim 1, wherein presentation comprises presentation of a graph of the flow rates over a period of time.

6. The method of claim 1, wherein presentation comprises presentation of a list of the flow rates and the respective corresponding times.

7. The method of claim 1, wherein presentation comprises presentation of a total flow over a period of time.

8. The method of claim 1, further comprising:
    receiving one or more flow-rate measurements; and
    outputting the flow-rate measurements for presentation.

9. The method of claim 1, further comprising:
    calculating and outputting for presentation a maximum estimated flow rate over a period of time.

10. The method of claim 1, further comprising:
    calculating a rate of change of flow-depth measurements over an elapsed period of time;
    making a rate-change determination that the calculated rate of change exceeds a rate-of-change threshold, and responsively outputting a rate-of-change alert via the user interface.

11. A system for estimating flow rates of a liquid in a conduit, the system comprising:
    a communication interface;
    a central processing unit; and
    a data storage containing program instructions executable by the central processing unit for:
        receiving one or more flow-depth measurements, each flow-depth measurement having been taken at a respective time;
        calculating a respective estimated flow rate for each of the one or more times, wherein each respective estimated flow rate is calculated based on at least (i) the corresponding flow-depth measurement and (ii) a set of one or more flow-estimation parameters each set to a respective initial value;
        outputting the estimated flow rates for presentation via a user interface;

receiving via the user interface one or more updated values, each received updated value corresponding to a respective one of the flow-estimation parameters;

calculating an updated estimated flow rate for each of the one or more times, wherein each respective updated estimated flow rate is calculated based on at least (i) the corresponding flow-depth measurement, (ii) the one or more received updated values, and (iii) respective initial values of any flow-estimation parameters for which no updated value was received; and outputting the updated estimated flow rates for presentation via the user interface.

12. The system of claim 11, wherein at least one of the flow-depth measurements comprises a measurement selected from a group of measurements consisting of an optical flow-depth measurement and an ultrasound flow-depth measurement.

13. The system of claim 11, wherein the set of flow-estimation parameters comprises a flow-depth-measurement offset.

14. The system of claim 11, wherein the set of flow-estimation parameters comprises one or more of a conduit radius, a conduit slope, and a roughness coefficient.

15. The system of claim 11, wherein presentation comprises presentation of a graph of the flow rates over a period of time.

16. The system of claim 11, wherein presentation comprises presentation of a list of the flow rates and the respective corresponding times.

17. The system of claim 11, wherein presentation comprises presentation of a total flow over a period of time.

18. The system of claim 11, further comprising:
receiving one or more flow-rate measurements; and
outputting the flow-rate measurements for presentation.

19. The system of claim 11, further comprising:
calculating and outputting for presentation a maximum estimated flow rate over a period of time.

20. The system of claim 11, further comprising:
calculating a rate of change of flow-depth measurements over an elapsed period of time;
making a rate-change determination that the calculated rate of change exceeds a rate-of-change threshold, and responsively outputting a rate-of-change alert via the user interface.

* * * * *